United States Patent
Saya et al.

(10) Patent No.: US 11,376,266 B2
(45) Date of Patent: Jul. 5, 2022

(54) ANTITUMOR AGENT

(71) Applicants: KEIO UNIVERSITY, Tokyo (JP); TOKYO INSTITUTE OF TECHNOLOGY, Tokyo (JP)

(72) Inventors: Hideyuki Saya, Tokyo (JP); Osamu Nagano, Tokyo (JP); Kenji Tsuchihashi, Tokyo (JP); Kentaro Suina, Tokyo (JP); Nobuhiro Nishiyama, Tokyo (JP); Hiroyasu Takemoto, Tokyo (JP); Takahiro Nomoto, Tokyo (JP); Makoto Matsui, Tokyo (JP); Keishiro Tomoda, Tokyo (JP); Naoki Yamada, Tokyo (JP); Tsukasa Nishimori, Tokyo (JP)

(73) Assignees: Keio University, Tokyo (JP); Tokyo Institute of Technology, Tokyo (JP)

( * ) Notice: Subject to any disclaimer, the term of this patent is extended or adjusted under 35 U.S.C. 154(b) by 762 days.

(21) Appl. No.: 16/067,906

(22) PCT Filed: Jan. 5, 2017

(86) PCT No.: PCT/JP2017/000184
§ 371 (c)(1),
(2) Date: Aug. 22, 2018

(87) PCT Pub. No.: WO2017/119462
PCT Pub. Date: Jul. 13, 2017

(65) Prior Publication Data
US 2020/0261476 A1    Aug. 20, 2020

(30) Foreign Application Priority Data
Jan. 6, 2016 (JP) .............................. JP2016-001128

(51) Int. Cl.
A61K 31/635 (2006.01)
A61K 47/60 (2017.01)
A61K 9/00 (2006.01)

(52) U.S. Cl.
CPC ............ *A61K 31/635* (2013.01); *A61K 47/60* (2017.08); *A61K 9/0019* (2013.01)

(58) Field of Classification Search
None
See application file for complete search history.

(56) References Cited

U.S. PATENT DOCUMENTS

| | | |
|---|---|---|
| 9,364,552 B2 | 6/2016 | Baik et al. |
| 2007/0036750 A1* | 2/2007 | Chou ........................ A61P 9/00 424/85.1 |
| 2014/0378410 A1 | 12/2014 | Baik et al. |

FOREIGN PATENT DOCUMENTS

| | | | | |
|---|---|---|---|---|
| JP | 2012-144498 A | | 8/2012 | |
| JP | 2012144498 A | * | 8/2012 | |
| JP | 2015-500334 A | | 1/2015 | |
| WO | WO-2014124487 A1 | * | 8/2014 | ............... A61P 9/14 |

OTHER PUBLICATIONS

International Search Report for International Application No. PCT/JP2017/000184 dated Mar. 28, 2017 (5 pages) (English language translation provided).
Written Opinion of the International Searching Authority for International Application No. PCT/JP2017/000184 dated Mar. 28, 2017 (4 pages) (English language translation not provided).
Gout et al., "Sulfasalazine, a potent suppressor of lymphoma growth by inhibition of the x(c)-cystine transporter: a new action for an old drug," Leukemia 15(10):1633-1640 (2001).
Li et al., "Current drug research on PEGlyation with small molecular agents," Prog Polym Sci. 38:421-444 (2013).
Pendri et al., "PEG modified anticancer drugs: synthesis and biological activity," J Bioact Compat Polym.11:122-134 (1996).
Extended European Search Report for European Patent Application No. 17735999.9, dated Aug. 7, 2019 (5 pages).
Rajesh et al., "Solubility enhancement, physicochemical characterization and in vivo evaluation of the anti-inflammatory activity of sulfasalazine in complex with beta-cyclodextrin," Research J Pharma and Tech. 5(1): 53-59 (2012).
Nikunj et al., "Formulation and evaluation of sulphasalazine injection made by mixed solvency solubilization technique," IRJP. 3(5):221-227 (2012).
Rajesh et al., "Enhanced solubility study of sulphasalazine using different solubilization techniques," IRJP. 3(8):187-190 (2012).

* cited by examiner

*Primary Examiner* — Layla Soroush
(74) *Attorney, Agent, or Firm* — Clark & Elbing LLP

(57) ABSTRACT

The present invention is directed to provide antitumor agent including water-soluble sulfasalazine as an active ingredient. Antitumor agents were obtained with, as the water-soluble sulfasalazine, a PEG-modified sulfasalazine represented by the following formula:

(1)

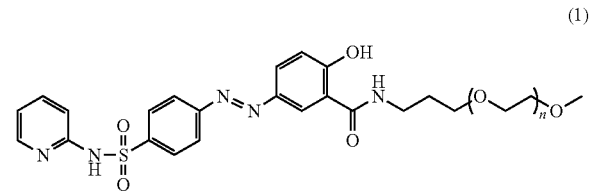

wherein an average value of n is 4 or larger and 1136 or smaller.

4 Claims, 6 Drawing Sheets

ANTITUMOR AGENT

CROSS REFERENCE TO RELATED APPLICATIONS

The present application claims priority of Japanese patent application No. 2016-001128 filed Jan. 6, 2016 and the disclosure thereof is hereby incorporated by reference.

TECHNICAL FIELD

The present invention relates to antitumor agents.

BACKGROUND ART

Expression of CD44v is observed in many epithelial tumors. Among cancer cells, CD44v is highly expressed in a population of cells called cancer stem cells which are known to have particularly high oxidative stress resistance.

Since CD44v increases the stability of the cystine transporter xCT, a cell surface molecule, high expression of CD44v enhances expression of xCT. As a result, transportation of cystine into cells is promoted. The transported cystine is used for the production of glutathione, a potent antioxidant in cells, and thus the content of glutathione is increased in the cells. This is believed to be responsible for a high ability to cope with oxidative stress and a high resistance to treatment of cancer cells (JP-A-2012-144498).

Sulfasalazine (also known as salazosulfapyridine, salazopyrin, and salicylazosulfapyridine), which is a drug used in the treatment of ulcerative colitis and rheumatoid arthritis, is an acidic azo compound of sulfapyridine and 5-aminosalicylic acid (5-ASA). When administered orally, sulfasalazine is metabolized into sulfapyridine and 5-aminosalicylic acid (5-ASA) by intestinal bacteria. For the diseases mentioned above, 5-ASA in particular is regarded as the primary active ingredient.

In recent years, however, it has been revealed that intact sulfasalazine before metabolic degradation has an inhibitory effect on xCT and is effective as an antitumor agent (Leukemia vol. 15, pp. 1633-1640, 2001). This means that, when sulfasalazine is added to cancer cells, transportation of cystine into cells by xCT is suppressed and the glutathione production is reduced; consequently, oxidative stress resistance of cancer cells is reduced and sensitivity to anticancer agents is increased.

It is, however, anticipated that an antitumor effect may be reduced if sulfasalazine is administered as a conventional oral agent, because intact sulfasalazine is effective for tumors. Accordingly, injections such as local injections of sulfasalazine are expected to be developed; however, sulfasalazine hardly soluble in water although it is soluble in sodium hydroxide solution or ethanol.

Therefore, the present invention was made aiming to provide antitumor agents containing water-soluble sulfasalazine as an active ingredient.

SUMMARY OF THE INVENTION

One aspect of the present invention is an antitumor agent including water-soluble sulfasalazine as an active ingredient, the water-soluble sulfasalazine being a PEG-modified sulfasalazine represented by the following formula:

[Chem 1]

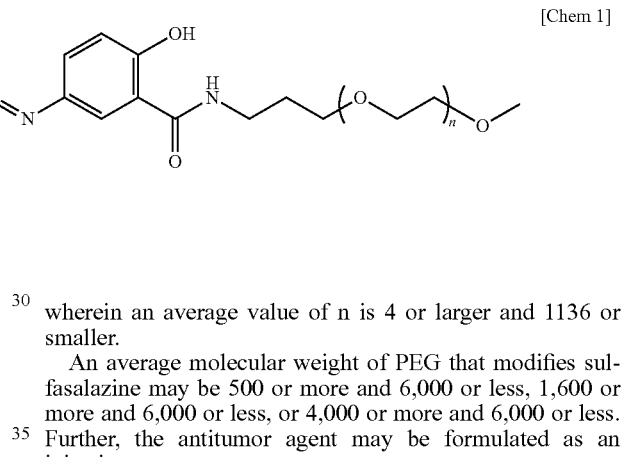

wherein an average value of n is 4 or larger and 1136 or smaller.

An average molecular weight of PEG that modifies sulfasalazine may be 500 or more and 6,000 or less, 1,600 or more and 6,000 or less, or 4,000 or more and 6,000 or less. Further, the antitumor agent may be formulated as an injection.

EMBODIMENTS OF THE INVENTION

Figure 1:
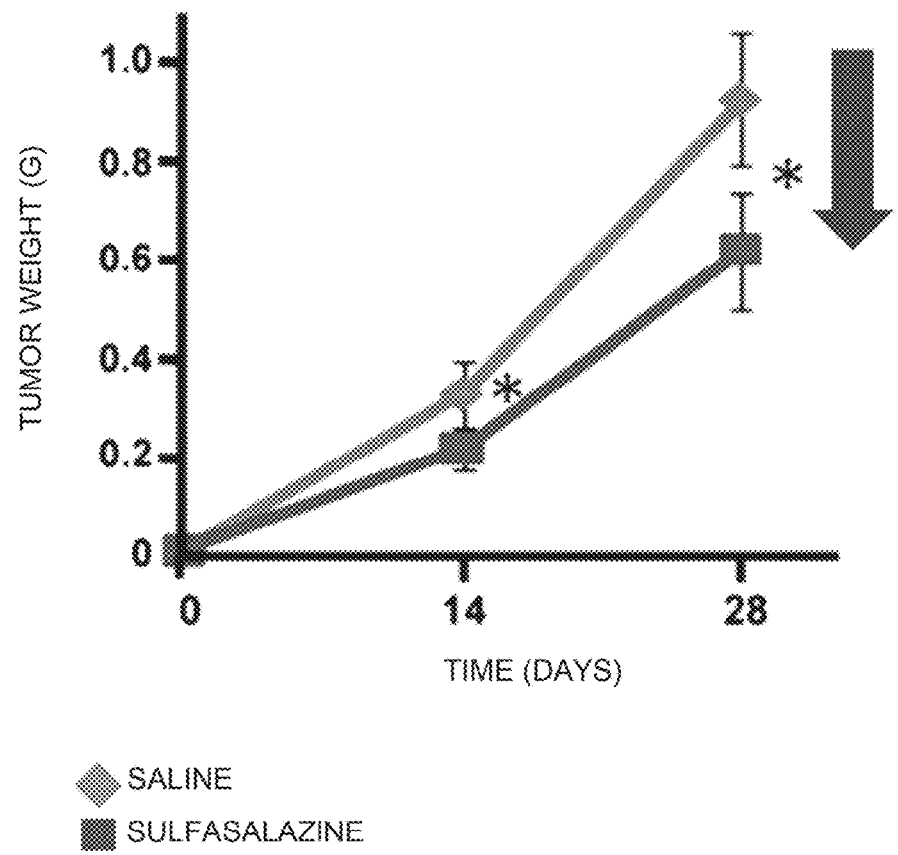
FIG. 1 is a graph showing an antitumor effect of sulfasalazine obtained in an Example of the present invention. The single asterisk (*) indicates p<0.05.

Embodiments of the present invention that was completed based on the findings mentioned above are described in detail below with reference to Examples. The objects, features, advantages, and ideas of the present invention are apparent to those skilled in the art from the description of this specification. Those skilled in the art can easily reproduce the present invention from the description herein. The embodiments and specific examples described below represent preferable aspects of the present invention, which are given for the purpose of illustration or explanation. The present invention is not limited thereto. It is obvious to those skilled in the art that various changes and modifications may be made according to the description of the present specification within the spirit and scope of the present invention disclosed herein.

==PEG-Modified Sulfasalazines==

An antitumor agent containing the water-soluble sulfasalazine of the present invention as an active ingredient is a PEG-modified sulfasalazine represented by the following formula:

[Chem 1]

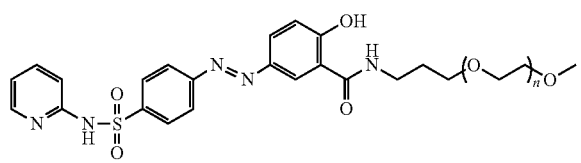

wherein an average value of n is preferably 4 or larger and 1136 or smaller, more preferably 20 or larger and 227 or smaller, and even more preferably 80 or larger and 136 or smaller.

The average molecular weight of PEG that modifies sulfasalazine is not particularly limited, but the lower limit is preferably 200, more preferably 500, even more preferably 1,000, further preferably 1,600, still further preferably 1,800, yet more preferably 4,000 or more, and yet further preferably 4,500 or more. The upper limit is preferably 50,000, more preferably 20,000, even more preferably 10,000, further preferably 6,000, and still further preferably 5,500.

PEG-modified sulfasalazines are produced by a chemical reaction between an end group of PEG molecule and sulfasalazine as described in <Production Example 1> and <Production Example 2>, but a specific method is not particularly limited and well-known techniques can be used. An outline of the production method is, for example, as follows. For the type-A PEGylated sulfasalazines, a terminal amino group of PEG and carboxylic acid of sulfasalazine are subjected to a condensation reaction. The type-B PEGylated sulfasalazine is produced by a nucleophilic substitution between a terminal iodine group of PEG and a hydroxyl group of sulfasalazine.

==Antitumor Agents==

The antitumor agent containing water-soluble sulfasalazine as an active ingredient may be formulated into any dosage form and various dosage forms can be considered; however, it is preferable that the antitumor agent is a parenteral agent. For example, the antitumor agent may be, but not limited to, an injection such as a subcutaneous injection, an intravenous injection, an intramuscular injection, or an intraperitoneal injection; an agent for transdermal administration or a patch, an ointment or a lotion; a sublingual agent for buccal administration or an oral patch; an aerosol agent for intranasal administration; or a suppository. These agents can be produced by a publicly known method which is commonly used in producing pharmaceutical products. The drug according to the present invention may be formulated in a sustained- or controlled-release dosage form.

Injections are particularly preferred, but local injections are more preferred, which can be injected in the vicinity of a tumor or into the tumor. The vicinity of tumor is preferably an area within about 5 cm, more preferably within about 3 cm, even more preferably within about 1 cm, and further preferably within about 0.5 cm from the outer surface of a tumor mass. Injections can be prepared for subcutaneous, intramuscular and intravenous injections using a well-known technique by adding a pH adjusting agent, a buffer, a stabilizer, an isotonizing agent, a local anesthetic agent and others to the active ingredient. In this preparation, examples of the pH adjusting agent and buffer include sodium citrate, sodium acetate, and sodium phosphate. Examples of the stabilizer include sodium pyrosulfite, ethylenediaminetetraacetic acid (EDTA), thioglycolic acid, and thiolactic acid. Examples of the local anesthetic agent include procaine hydrochloride and lidocaine hydrochloride. Examples of the isotonizing agent include sodium chloride and glucose.

The amount of the active ingredient contained in the medicine can be appropriately determined depending on, for example, a dose range of the active ingredient and the number of dosing. The dose range for administration is not particularly limited and can be appropriately selected depending on effectiveness of ingredients contained, a mode of administration, a route of administration, the type of disease, attributes of a subject (e.g., body weight, age, medical conditions and the presence or absence of the use of other medicines), and judgment of a physician in charge. Generally, an appropriate dose is preferably, for example, in the range of about 0.01 μg to 100 mg, preferably about 0.1 μg to 1 mg per 1 kg of the subject's body weight. These doses, however, can be modified using conventional routine experiments for optimization well known in the art. The above dosage can be administered once to several times a day.

EXAMPLES (1) Antitumor Effect of Sulfasalazine

The human colon cancer HCT-116 cells that proliferate in a CD44v-dependent manner were administered subcutaneously to KSN nude mice to form tumors. The cells were transplanted into 10 mice. 250 mg/kg of sulfasalazine or 100 μl of saline was injected to each of groups of 5 mice intraperitoneally once per day. Diameter of tumors was measured on Days 14 and 28 after transplantation and their weights were calculated based on the diameters and compared between the two groups.

As shown in FIG. 1, tumor growth was significantly slower in the sulfasalazine group than in the control group. Thus, sulfasalazine has an inhibitory effect on tumor growth.

(2) Synthesis of PEG-Modified Sulfasalazines

Figure 2:
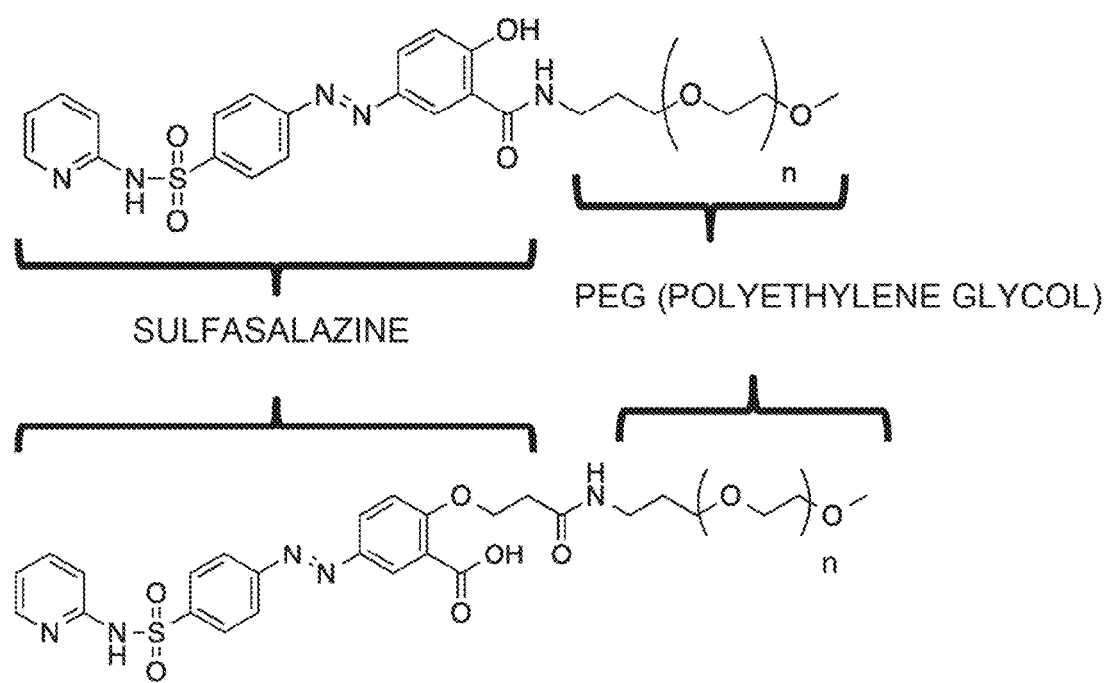
FIG. 2 shows structural formulae of PEGylated sulfasalazines used in Examples. The upper formula is referred to as type A, and the lower formula is referred to as type B.

In this example, a type-A PEGylated sulfasalazine shown in the upper half of FIG. 2 and a type-B PEGylated sulfasalazine shown in the lower half of the figure were synthesized.

Figure 3:
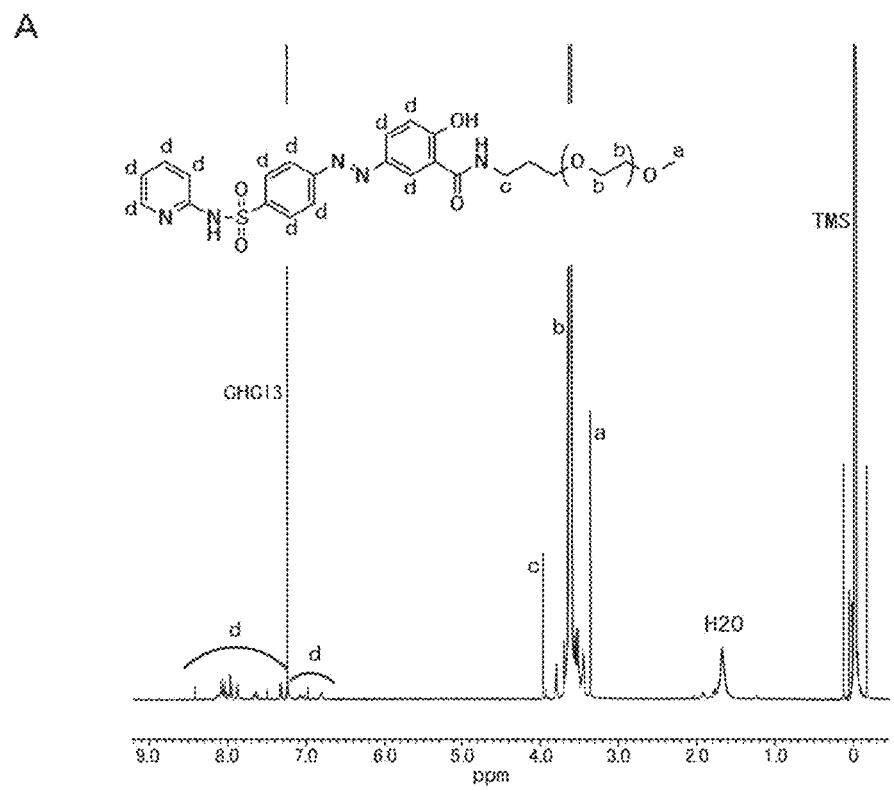
FIG. 3 is graphs showing results of NMR analysis of type-A and type-B PEGylated sulfasalazines produced in an Example of the present invention.
Figure 3:
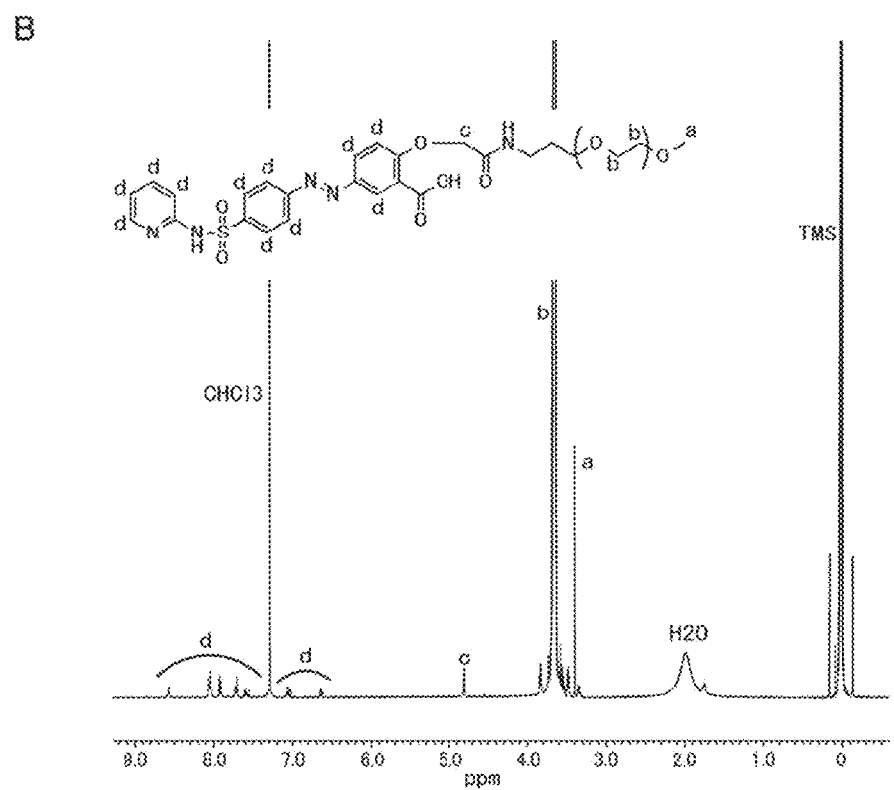

<Production Example 1> Production of Type-A PEGylated Sulfasalazine 500 mg of α-Methoxy-ω-amino-poly(ethylene glycol) (average molecular weight: 5000 Da) [NOF CORPORATION, SUNBRIGHT PA (trade name), CAS Registry Number: 116164-53-5] was dissolved in 20 mL of tetrahydrofuran and mixed with 300 mg of DMT-MM (4-(4,6-dimethoxy-1,3,5-triazin-2-yl)-4-methylmorpholinium chloride) [CAS Registry No. 3945-69-5] and 400 mg of sulfasalazine; and then the mixture was stirred at 50° C. for 24 hours. Tetrahydrofuran in the solution thus obtained was distilled off under reduced pressure and the residue was resuspended in 10 mL of 0.01 M hydrochloric acid. The suspension was centrifuged at 20,000 g for 60 minutes at 4° C. The supernatant was subjected to liquid separation using a saturated aqueous ammonium chloride solution and methylene chloride, extracted with the methylene chloride layer, and then the solvent was distilled off under reduced pressure. The resultant solid was dissolved in pure water, purified on a PD-10 column, and lyophilized to obtain yellow powder as a desired product (type-A PEGylated sulfasalazine) (yield: 450 mg). FIG. 3A shows a result of an NMR measurement.

<Production Example 2> Production of Type-B PEGylated Sulfasalazine 300 mg of α-iodoacetamidopropyl-ω-methoxy-poly (ethylene glycol) was dissolved in 5 mL of DMF and 100 mg of cesium carbonate was then suspended in the solution. 63 mg of sulfasalazine was further added, and the mixture was stirred at 50° C. overnight. The reaction solution was purified by dialysis against methanol, the solvent was distilled off under reduced pressure, and the residue was resuspended in 10 mL of 0.01 M hydrochloric acid. The suspension was centrifuged at 20,000 g for 60 minutes at 4° C. The supernatant was purified on a PD-10 column and lyophilized to obtain yellow powder as a desired product (type-B PEGylated sulfasalazine) (yield: 270 mg). FIG. 3B shows a result of an NMR measurement.

(3) Measurement of the Amount of Exported Glutamate

Sulfasalazine has an inhibitory effect on xCT. When added to cancer cells, sulfasalazine suppresses transportation of cystine into cells by xCT. Since the transporter xCT exports glutamate in parallel with the cystine uptake, it is possible to examine an inhibitory activity of sulfasalazine on xCT by examining suppression of glutamate export. Thus, in this Example, inhibitory activities of PEGylated sulfasalazines on xCT were examined by measuring the amount of exported glutamate.

Using DMEM (Nacalai Tesque, 08459-64; note that DMEM was supplemented with glutamate and 10% FBS, and was antibiotic-free), a head and neck squamous cell carcinoma cell line OSC 19 was seeded onto 6-well plates at 200,000 cells/well. After 12 hours, the cells that had adhered to the bottom of the plates were washed twice with DMEM and the medium was then replaced with 2 mL of glutamic acid-free medium containing sulfasalazine or 400 μM (calculated in amounts of sulfasalazine) of PEGylated sulfasalazines (the type-A PEGylated sulfasalazines PEGylated with PEG 2000 or PEG 5000 and the type-B PEGylated sulfasalazine PEGylated with PEG5000). After 8 hours, the content of glutamate in the medium was measured based on absorbance using a Glutamate assay kit (manufactured by Abcam plc.). It should be noted that the absorbance of the drug-free medium itself was measured and subtracted, as a background, from measured absorbances obtained with the drugs-supplemented mediums or the drug-free medium after the cell culture to obtain glutamate contents. Then, each value was calculated as a ratio to the value for the drug-free control defined as 1 and the results were graphed (FIG. 4).

Figure 4:
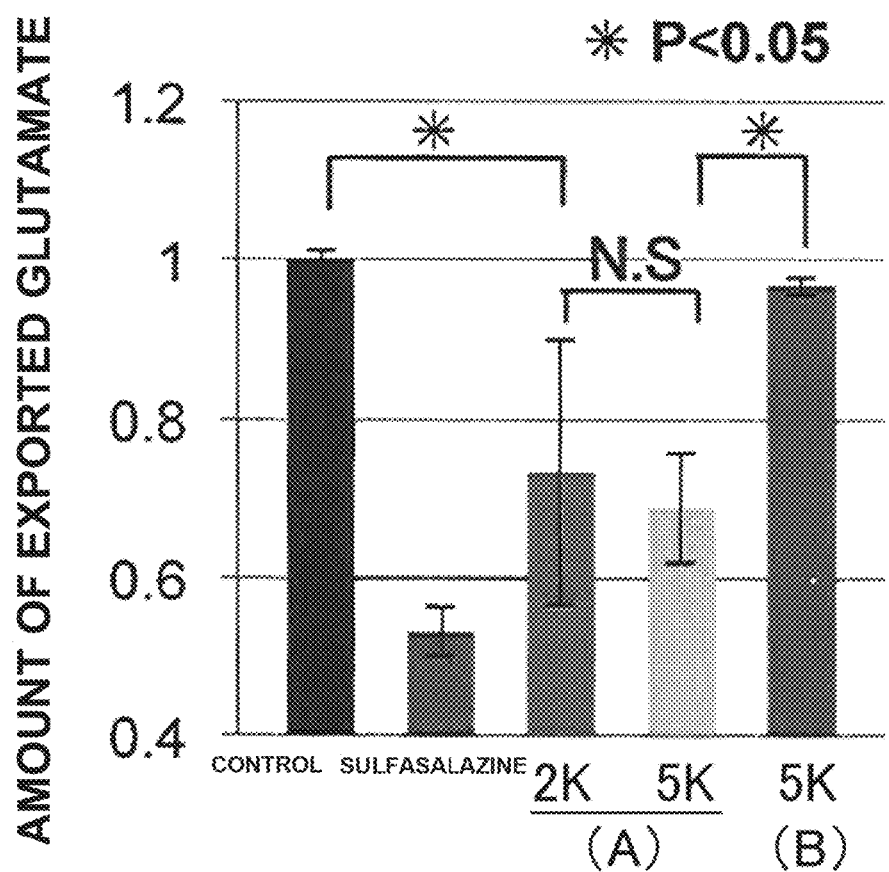
FIG. 4 is a graph showing a suppression of glutamate export by a type-A PEGylated sulfasalazine obtained in an Example of the present invention. The single asterisk (*) indicates p<0.05.

As is obvious from the graph in FIG. 4, both of the type-A PEGylated sulfasalazines PEGylated with PEG 2000 or PEG 5000 significantly suppressed the glutamate export compared with the drug-free control. Further, they also significantly suppressed the glutamate export compared with the type-B PEGylated sulfasalazine.

Thus, the type-A PEGylated sulfasalazines have an inhibitory activity on xCT although it is a little weaker than that of sulfasalazine. In contrast, the type-B PEGylated sulfasalazine has no inhibitory activity on xCT.

(4) Measurement of Active Oxygen Species in Cells

Sulfasalazine has an inhibitory effect on xCT and suppresses transportation of cystine into cells by xCT when added to cancer cells. Cystine is converted into reduced glutathione in cells. Since the reduced glutathione functions to suppress an increase in active oxygen species in cells, the inhibition of xCT leads to an increase in active oxygen species; therefore, it is possible to examine an inhibitory activity of sulfasalazine on xCT by examining the content of active oxygen species in cells. Accordingly, in this Example, inhibitory activities of PEGylated sulfasalazines on xCT were examined by measuring contents of active oxygen species in cells.

Using the same medium as in (3), the OSC 19 cell line was seeded onto 96-well plates at 4,000 cells/well. On the next day, sulfasalazine or the type-A PEGylated sulfasalazines were added at 400 μM (calculated in amounts of sulfasalazine). After 24 hours, a fluorescence intensity of CM-H2DCFDA which is a chloromethyl derivative of H2DCFDA was measured with a plate reader as a level of active oxygen species in cells. H2DCF portion of CM-H2DCFDA is quickly oxidized into DCF by reacting with hydrogen peroxide, hydroxyl radicals, peroxynitrite and others in cells and emits fluorescence. Accordingly, fluorescence intensities can be used as indications of the level of active oxygen species in cells. In addition, the number of cells was measured by the fluorescence intensity of Hoechst 33342. Since Hoechst 33342 stains the nucleus, its fluorescence intensity is proportional to the number of cells. Then, a level of active oxygen species per cell in each well was calculated as a ratio of CM-H2DCFDA/Hoechst 33342. Relative values of levels of active oxygen species in the groups of cells treated with the drug to its level in cells of the drug-free control were calculated by defining the latter as 1 and the results were graphed (FIG. 5).

Figure 5:
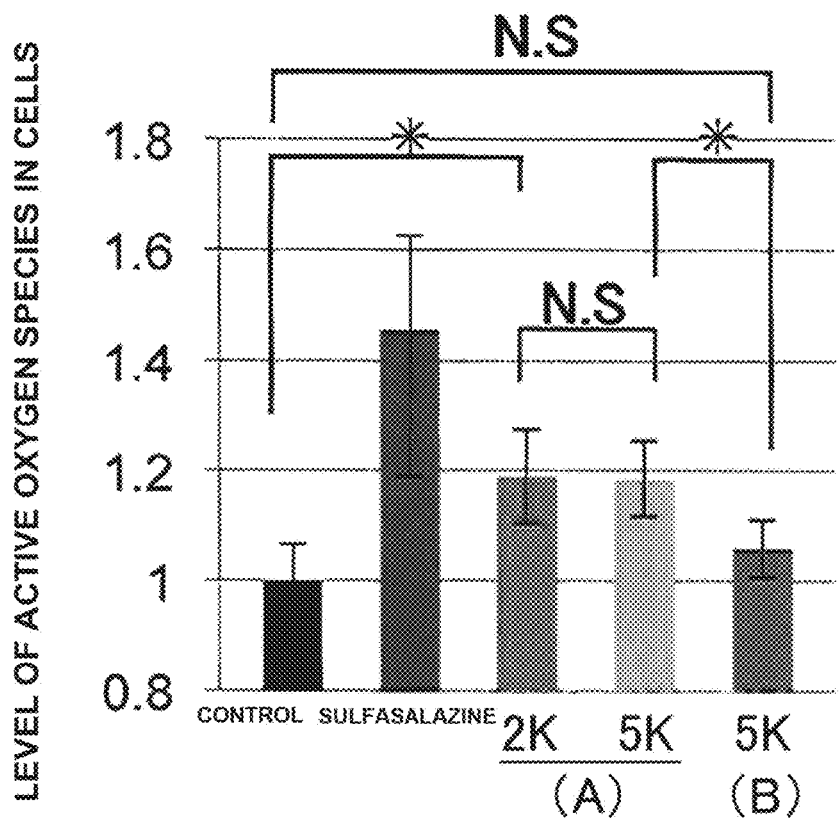
FIG. 5 is a graph showing an increase of active oxygen level in cells by a type-A PEGylated sulfasalazine obtained in an Example of the present invention. The single asterisk (*) indicates p<0.05.

As is obvious from the graph of FIG. 5, both of the type-A PEGylated sulfasalazines PEGylated with PEG 2000 or PEG 5000 significantly enhanced the level of active oxygen species in cells compared with the drug-free control. Further, they also significantly enhanced the level of active oxygen species in cells compared with the type-B PEGylated sulfasalazine.

Thus, the type-A PEGylated sulfasalazine enhances the level of active oxygen species in cells although it is a little weaker than that of sulfasalazine. In contrast, the type-B PEGylated sulfasalazine does not enhance the level of active oxygen species in cells.

(5) Cell Viability Assay

In this Example, cytotoxicity of the type-A PEGylated sulfasalazines (PEGylated with PEG 2000 or PEG 5000) at different concentrations was compared with that of sulfasalazine.

Using the same medium as in (3), the T98G cell line was seeded onto 96-well plates at 3,000 cells/well. On the next day, sulfasalazine and the type-A PEGylated sulfasalazines were added at 0 to 1250 µM calculated in concentrations of sulfasalazine. Two days later, cell viability was measured using a CellTiter-Glo (Promega). Viability at each concentration was determined as a proportion to the viability (100%) of the drug-free control (0 µM) and the results were graphed (FIG. 6).

Figure 6:
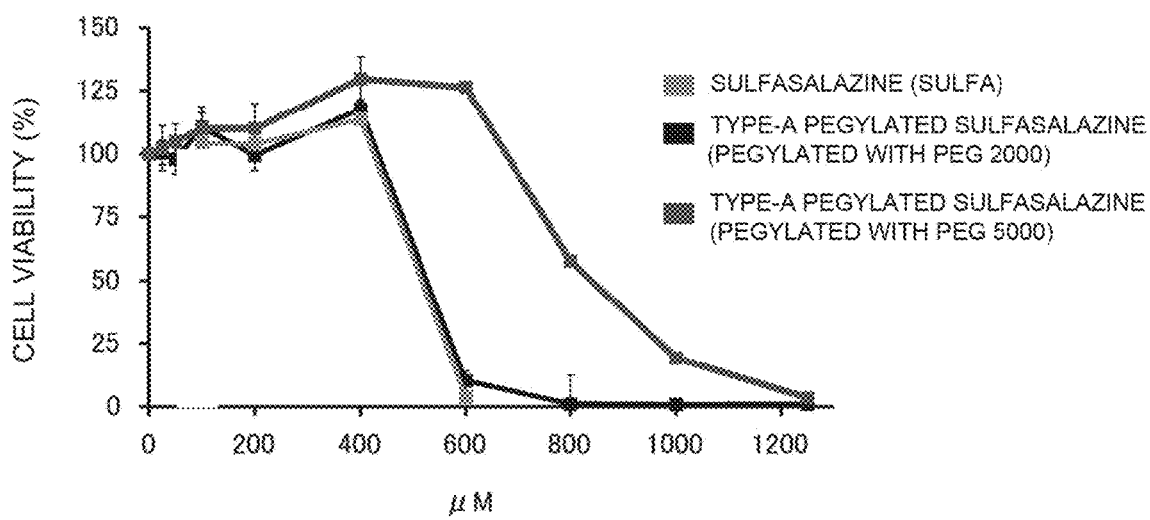
FIG. 6 is a graph showing concentration dependency of cytotoxicity of a type-A PEGylated sulfasalazine in an Example of the present invention.

As is obvious from the graph of FIG. 6, the cell viability increased in all cases up to 400 µM. Sulfasalazine and the type-A PEGylated sulfasalazine (PEGylated with PEG 2000) showed substantially identical concentration dependence, but the type-A PEGylated sulfasalazine (PEGylated with PEG 5000) resulted in a higher cell viability than the sulfasalazine and the type-A PEGylated sulfasalazine (PEGylated with PEG 2000) at concentrations higher than 400 µM.

Thus, the type-A PEGylated sulfasalazine (PEGylated with PEG 5000) increases cell viability but the type-A PEGylated sulfasalazine (PEGylated with PEG 2000) still results in cell viability comparative to that obtained with sulfasalazine.

(6) Solubility Test for Sulfasalazine and PEGylated Sulfasalazines 10 mg of sulfasalazine in powder form and 25 mg of the type-A PEGylated sulfasalazine which had been PEGylated with PEG 5000 were dissolved in 100 µL of pure water and saline. At this time, it was observed that some sulfasalazine powder was left undissolved in the aqueous solutions at room temperature, based on which sulfasalazine was considered to be saturated. The type-A PEGylated sulfasalazine was completely dissolved and no undissolved portion was left. The aqueous solutions thus obtained were centrifuged at 8000 rpm for 30 minutes at room temperature, and 50 µL of each supernatant was taken. One microliter of 5N NaOH solution was added to the supernatant and UV absorption (at 238 nm) was measured for the resulting solution, thereby sulfasalazine concentration in the solution (solubility in pure water and saline) was calculated.

As shown in Table 1, the saturated solubilities of sulfasalazine in water and saline at room temperature were 0.050 mg/mL and 0.037 mg/mL, respectively. These solubilities could be increased to at least 20.5 mg/mL and 19.1 mg/mL, respectively, at room temperature by PEGylating sulfasalazine into the type-A PEGylated sulfasalazine.

TABLE 1

| Saturated solubility of sulfasalazine (mg/mL) | | |
|---|---|---|
| | Pure water | Saline |
| Sulfasalazine | 0.050 mg/mL | 0.037 mg/mL |
| Type-A PEGylated sulfasalazine | ≥20.5 mg/mL | ≥19.1 mg/mL |

* The saturated solubilities of the type-A PEGylated sulfasalazine were values calculated as sulfasalazine (7) Evaluation of Antitumor Activity of Type-A PEGylated Sulfasalazines (PEGylated with PEG 500, PEG 1000, PEG 2000, or PEG 5000)

In this Example, effects of an average molecular weight of PEG used for PEGylating sulfasalazine on antitumor activity were evaluated.

Figure 7:
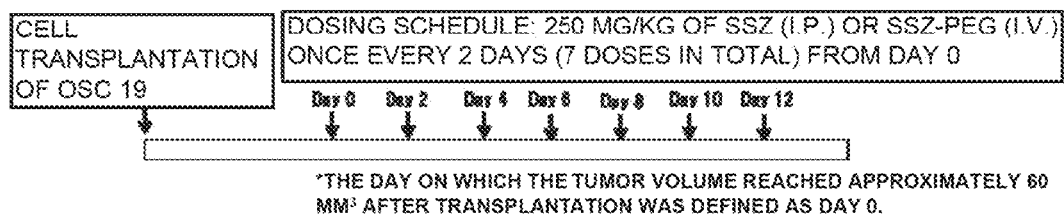
FIG. 7 shows a dosing schedule of sulfasalazine to tumor-bearing mice used in an Example of the present invention.
Figure 8:
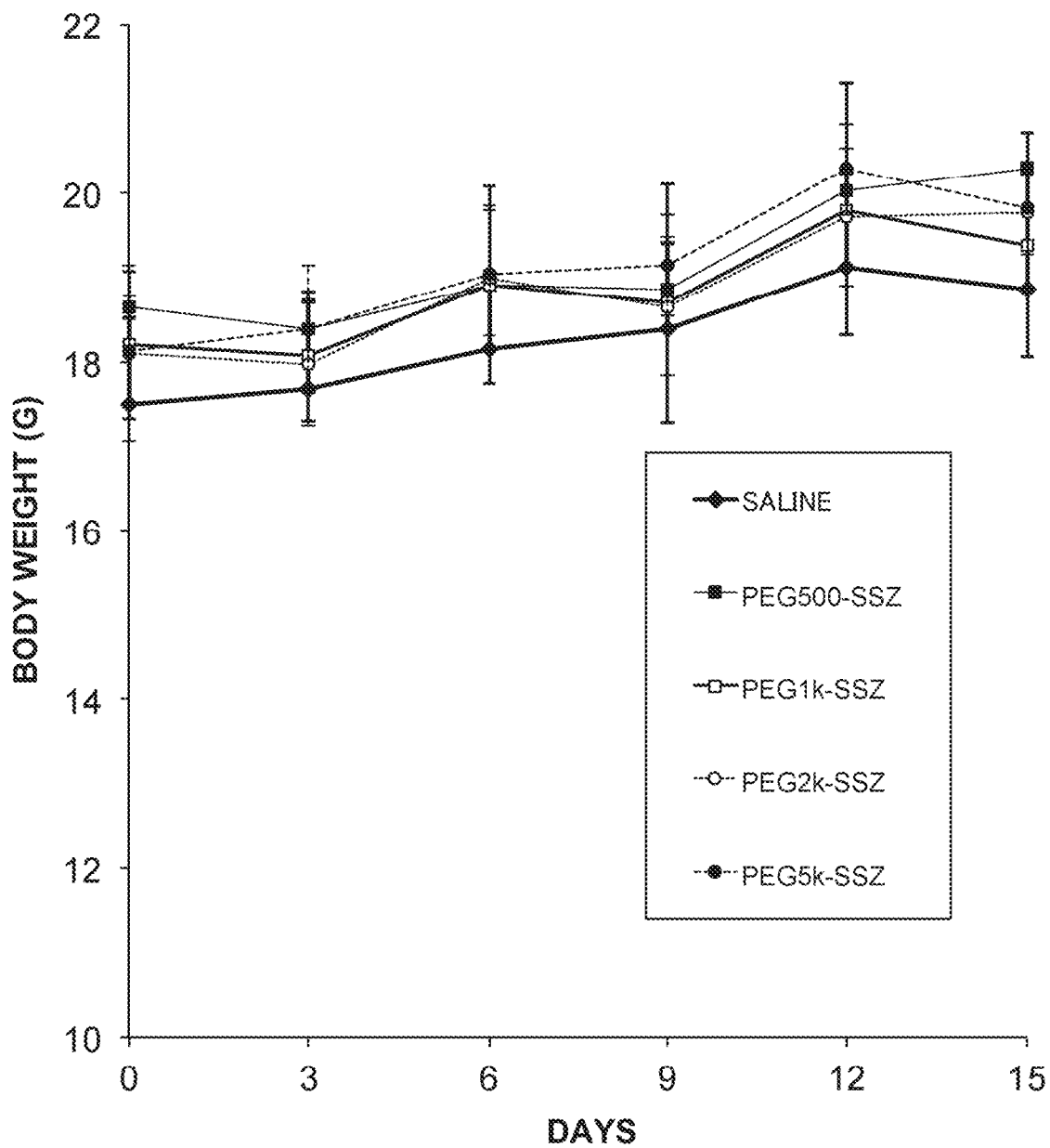
FIG. 8 is a graph showing transitions of average body weights of tumor-bearing mice from the first day of dosing of type-A PEGylated sulfasalazines (PEGylated with PEG 500, PEG 1000, PEG 2000, or PEG 5000) in an Example of the present invention.
Figure 9:
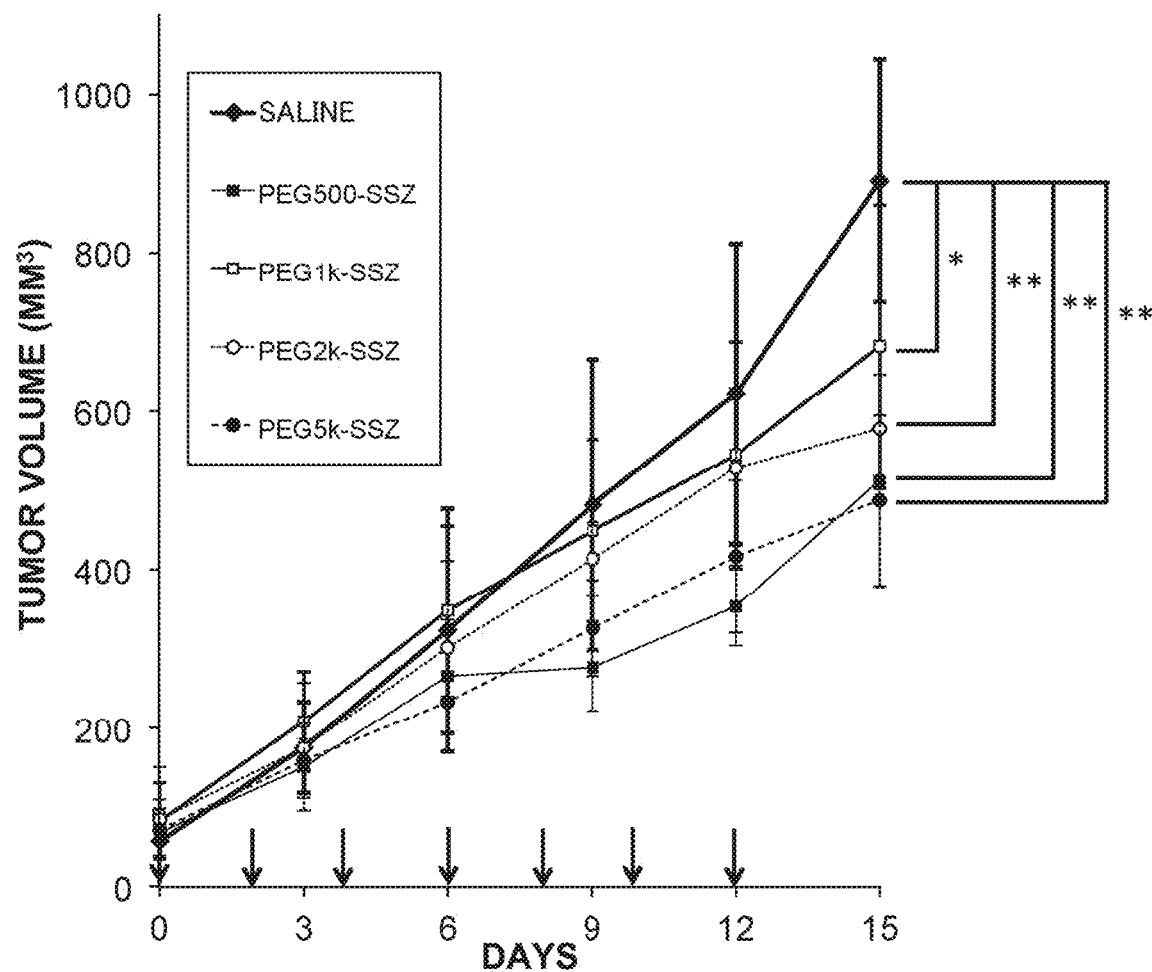
FIG. 9 is a graph showing transitions of average volumes of tumors in tumor-bearing mice from the first day of dosing of type-A PEGylated sulfasalazines (PEGylated with PEG 500, PEG 1000, PEG 2000, or PEG 5000) in an Example of the present invention. The single asterisk (*) indicates $p<0.05$ and the double asterisk (**) indicates $p<0.001$.

A cell suspension containing $1 \times 10^6$ OSC 19 cells was transplanted subcutaneously into the back of 4-week-old female mice (balb/c nu/nu) to form tumor. After 6 days of transplantation, at the time when the tumor volume reached approximately 60 mm$^3$, 25 mice transplanted with the cells were divided into 5 groups (5 animals per group) and each group was administered with the type-A PEGylated sulfasalazines (PEGylated with PEG 500, PEG 1000, PEG 2000, or PEG 5000) or saline. First, each of 11.3 mg of type-A PEG-500-PEGylated sulfasalazine (i.e., sulfasalazine PEGylated with PEG 500), 17.6 mg of type-A PEG-1000-PEGylated sulfasalazine (i.e., sulfasalazine PEGylated with PEG 1000), 30.1 mg of type-A PEG-2k-PEGylated sulfasalazine (i.e., sulfasalazine PEGylated with PEG 2000), and 67.8 mg of type-A PEG-5k-PEGylated sulfasalazine (PEGylated with PEG 5000) were dissolved in saline to prepare injections of 31.5 mM solution (calculated in concentrations of sulfasalazine). According to dosing schedule shown in FIG. 7, the prepared type-A PEGylated sulfasalazine injection with a single dose of the prepared drug of 400 µl (i.e., 250 mg/ml when calculated in amounts of sulfasalazine) or a saline injection was intravenously injected once every 2 days per group. The dosing frequency was set to 7 times in total (the first day of administration was set to Day 0, and after 0, 2, 4, 6, 8, 10, and 12 days from the first dosing). After 0, 3, 6, 9, 12, and 15 days from the first dosing, the body weight of each tumor-bearing mouse as well as long and short diameters of each tumor observed from outside were measured, and a volume of tumor was calculated based on the measured diameters of tumor. FIGS. 8 and 9 show graphs of transitions of average body weight (FIG. 8) and average volume of tumor (FIG. 9) in each group from the first day of dosing.

As shown in FIG. 8, since no significant change in body weight was observed in all groups, it was confirmed that the type-A PEGylated sulfasalazines administered were not toxic. Further, as shown in FIG. 9, it was confirmed that, in all groups administered with type-A PEGylated sulfasalazines, significantly higher antitumor activities than those in the group administered with saline could be observed 15 days after the first dosing.

Thus, irrespective of the average molecular weight of PEG used to PEGylate sulfasalazine, PEG-modified sulfasalazines have an antitumor activity.

INDUSTRIAL APPLICABILITY

According to the present invention, it became possible to provide antitumor agents containing water-soluble sulfasalazine as an active ingredient.

The invention claimed is:

1. A method for treating a patient with a tumor, comprising administering an effective amount of water-soluble sulfasalazine, the water-soluble sulfasalazine being a PEG-modified sulfasalazine represented by the following formula:

[Chem 1]

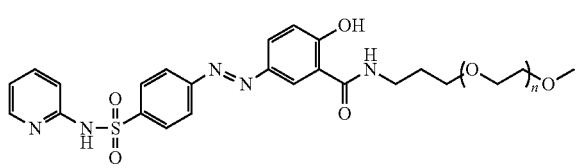

wherein an average value of n is 4 or larger and 1136 or smaller.

2. The method according to claim 1, wherein an average molecular weight of PEG that modifies sulfasalazine is 500 or more and 6,000 or less.

3. The method according to claim 1, wherein an average molecular weight of PEG that modifies sulfasalazine is 4,000 or more and 6,000 or less.

4. The method according to claim 1, wherein the water-soluble sulfasalazine is injected to the patient.

* * * * *